(12) United States Patent
Bao et al.

(10) Patent No.: US 9,140,624 B2
(45) Date of Patent: Sep. 22, 2015

(54) SYSTEMS AND METHODS REDUCING COHERENCE EFFECT IN NARROW LINE-WIDTH LIGHT SOURCES

(75) Inventors: Jun Bao, Ellicott City, MD (US); Michael Haidar Shahine, Ellicott City, MD (US); Hua Jiao, Ellicott City, MD (US); Jean-Luc Archambault, Severna Park, MD (US)

(73) Assignee: Ciena Corporation, Hanover, MD (US)

( * ) Notice: Subject to any disclaimer, the term of this patent is extended or adjusted under 35 U.S.C. 154(b) by 12 days.

(21) Appl. No.: 13/541,146

(22) Filed: Jul. 3, 2012

(65) Prior Publication Data

US 2014/0009763 A1    Jan. 9, 2014

(51) Int. Cl.
*G01N 21/55* (2014.01)
*G01M 11/00* (2006.01)

(52) U.S. Cl.
CPC .......... *G01M 11/3118* (2013.01); *G01N 21/55* (2013.01)

(58) Field of Classification Search
CPC .......... G01N 21/55; G01N 21/00; G02F 1/01
USPC ................. 356/73, 73.1, 447; 372/22; 398/25
See application file for complete search history.

(56) References Cited

U.S. PATENT DOCUMENTS

| | | |
|---|---|---|
| 5,179,420 A | 1/1993 | So et al. |
| 5,448,059 A | 9/1995 | Blank et al. |
| 5,771,250 A | 6/1998 | Shigehara et al. |
| 5,875,273 A | 2/1999 | Mizrahi et al. |
| 5,943,152 A | 8/1999 | Mizrahi et al. |
| 6,046,797 A | 4/2000 | Spencer et al. |
| 6,122,043 A | 9/2000 | Barley |
| 6,519,026 B1 * | 2/2003 | Holland ....................... 356/73.1 |
| 6,542,228 B1 | 4/2003 | Hartog |
| 6,618,193 B1 | 9/2003 | Boertjes |
| 7,042,559 B1 * | 5/2006 | Frigo et al. .................. 356/73.1 |
| 7,420,666 B2 | 9/2008 | Maehara et al. |
| 7,471,710 B2 | 12/2008 | Cliche et al. |
| 7,946,341 B2 | 5/2011 | Hartog et al. |
| 7,957,436 B2 | 6/2011 | Chen et al. |
| 8,477,296 B2 * | 7/2013 | Donlagic et al. ............. 356/73.1 |
| 2003/0210387 A1 * | 11/2003 | Saunders et al. ................ 356/73 |
| 2008/0144678 A1 * | 6/2008 | Lu et al. .......................... 372/22 |
| 2010/0119225 A1 * | 5/2010 | Snawerdt ........................ 398/25 |
| 2011/0134940 A1 | 6/2011 | Hartog |
| 2011/0260800 A1 | 10/2011 | Shanfield et al. |

* cited by examiner

*Primary Examiner* — Tarifur Chowdhury
*Assistant Examiner* — Jamil Ahmed
(74) *Attorney, Agent, or Firm* — Clements Bernard PLLC; Christopher L. Bernard; Lawrence A. Baratta, Jr.

(57) ABSTRACT

Systems and methods are described for reducing coherence effect in narrow line-width light sources through various modulation techniques. The systems and methods can include a narrow line-width laser source with a thermoelectric cooler thermally coupled thereto and a controller communicatively coupled to the thermoelectric cooler. The controller is configured to provide a varied input signal to the thermoelectric cooler to reduce coherence of the narrow line-width laser source by artificially broadening the narrow line-width on a time averaged basis. The systems and methods can also include direct modulation of the narrow line-width laser source. The systems and methods can include a narrow line-width Optical Time Domain Reflectometer (OTDR). The systems and methods can also include direct modulation of the narrow line-width laser source with or without the varied input signal to the thermoelectric cooler.

14 Claims, 10 Drawing Sheets

SYSTEMS AND METHODS REDUCING COHERENCE EFFECT IN NARROW LINE-WIDTH LIGHT SOURCES

FIELD OF THE INVENTION

Generally, the field of art of the present disclosure pertains to optical systems and methods, and more particularly, to systems and methods reducing coherence effect in narrow line-width light sources through various modulation techniques.

BACKGROUND OF THE INVENTION

As optical fiber capacity grows, it is becoming important to monitor and detect transmission degradations in optical fiber in real time. In an exemplary embodiment, more and more optical systems are relying on Raman amplification to extend reach, distance, and/or capacity. This requires optical fiber that exhibits good qualities as a transmission medium, i.e. low back reflection, low connector loss, etc. Conventional monitoring systems and methods can utilize commercial Optical Time Domain Reflectometers (OTDRs). Conventional OTDRs use broad spectrum light sources such as Fabry-Perot lasers that have multiple longitudinal lasing modes. Disadvantageously, conventional OTDRs are bulky and exhibit high cost. To reduce cost, it is possible to use Integrable Tunable Laser Assembly (ITLA), Externally Modulated Laser (EML), Distributed Feedback (DFB), or the like as a source to make an on-board, low cost OTDR-like monitoring device to perform optical fiber quality checks. However, due to narrow line-width (in the range of few hundred kHz to a few MHz) of ITLA, EML, DFB, etc. sources, this narrow line-width causes coherence effects in detected Rayleigh scattering signals making the OTDR measurements unreliable. There exists a need for a simple approach in reducing the coherence effects due to narrow line-width from ITLA, EML, DFB, etc. sources.

BRIEF SUMMARY OF THE INVENTION

In an exemplary embodiment, an optical time domain reflectometer (OTDR) system includes a narrow line-width laser source comprising a thermoelectric cooler thermally coupled thereto; a modulator configured to modulate the narrow line-width laser source; a device coupling an output of the narrow line-width laser source and the modulator to a device under test and an input from the device under test to a photodetector; and a controller providing an input signal to the thermoelectric cooler; wherein the optical time domain reflectometer system utilizes one of direct modulation and dithering of the thermoelectric cooler by the controller, and wherein each of the direct modulation and the dithering reduce noise in OTDR traces to comparable levels of a wide spectrum laser source OTDR. The modulator can include an external modulator, and the input signal can be varied to the thermoelectric cooler to reduce coherence of the narrow line-width laser source. Optionally, the modulator can directly modulate the narrow line-width laser source. The input signal is varied to the thermoelectric cooler to reduce the effects of the coherence of the narrow line-width laser source. The controller can be configured to adjust the varied input signal at a predetermined frequency and for predetermined amount of change in the thermoelectric cooler. Optionally, the narrow line-width laser source can include a line-width of 10 MHz or less with a time averaged line-width artificially broadened responsive to the varied input signal to the thermoelectric cooler. The narrow line-width laser source can include one of an Integrable Tunable Laser Assembly (ITLA), an Externally Modulated Laser (EML), and a Distributed Feedback (DFB) laser. The narrow line-width laser source, the thermoelectric cooler, and the controller can be disposed in an optical device in an optical communication system and can be collectively configured to perform Optical Time Domain Reflectometer functionality in the optical communication system. The optical device can include one of a service channel, an amplifier, and a channel line card.

In another exemplary embodiment, an optical apparatus includes a narrow line-width laser source; a thermoelectric cooler thermally coupled to the narrow line-width laser source; and a controller communicatively coupled to the thermoelectric cooler and configured to provide a varied input signal to the thermoelectric cooler to reduce the effects of coherence of the narrow line-width laser source, wherein the controller is configured to adjust the varied input signal at a predetermined frequency and for predetermined amount of change in the thermoelectric cooler. The narrow line-width laser source can include a line-width of 10 MHz or less with a time averaged line-width artificially broadened responsive to the varied input signal to the thermoelectric cooler. The narrow line-width laser source can include one of an Integrable Tunable Laser Assembly (ITLA), an Externally Modulated Laser (EML), and a Distributed Feedback (DFB) laser. The narrow line-width laser source, the thermoelectric cooler, and the controller can be disposed in an optical communication system and can be collectively configured to perform Optical Time Domain Reflectometer functionality in the optical communication system.

In yet another exemplary embodiment, an optical method includes outputting a laser signal from a narrow line-width source at a first line-width; modifying a thermoelectric cooler thermally coupled to the narrow-line width laser source at a predetermined amount over a predetermined frequency; and outputting the laser signal from the narrow line-width source at a second line-width that is artificially broadened on a time average basis relative to the first line-width thereby reducing coherence of the narrow line-width source.

In yet another exemplary embodiment, an optical system includes a first optical node communicatively coupled to a second optical node, wherein the first optical node includes at least one narrow line-width source, wherein the at least one narrow line-width source includes a thermoelectric cooler thermally coupled thereto; a modulator configured to modulate the at least one narrow line-width source; and a controller providing an input signal to the thermoelectric cooler; wherein at least one narrow line-width source is configured to perform optical time domain reflectometer (OTDR) functionality between the first optical node and the second optical node, wherein the first optical node utilizes one of direct modulation of the at least one narrow line-width source by the modulator and dithering of the thermoelectric cooler by the controller, and wherein each of the direct modulation and the dithering reduce noise in OTDR traces to comparable levels of a wide spectrum laser source OTDR. The at least one narrow line-width source can include a wavelength outside of an amplification band of amplifiers between the first optical node and the second optical node. The at least one narrow line-width source can be a monitor wavelength of a Raman amplifier between the first optical node and the second optical node.

BRIEF DESCRIPTION OF THE DRAWING(S)

Exemplary and non-limiting embodiments of the present disclosure are illustrated and described herein with reference to various drawings, in which like reference numbers denote like method steps and/or system components, respectively, and in which.

DETAILED DESCRIPTION OF THE INVENTION

In various exemplary embodiments, the present disclosure relates to systems and methods for reducing coherence effect in narrow line-width light sources through various modulation techniques. In an exemplary embodiment, the narrow line-width light sources can include ITLA, EML, DFB, etc. lasers with a reduction of the coherence effect by increasing the line-width through modulating the drive signal of the thermoelectric cooler (TEC) of the light sources. This modulation of the TEC can shift the center wavelength of light source (e.g., randomly, in a predetermined fashion, etc.). The coherence effect can be effectively canceled out by averaging the measurements. This approach allows the use of narrow line-width source such as ITLA, EML, DFB, etc. lasers as OTDR-like sources in an integrated function in optical fiber communication system to monitor fiber behavior in real-time. In another exemplary embodiment, the narrow line-width light sources can be directly modulated in the OTDR application providing a reduction of the coherence effect relative to external modulation. In yet another exemplary embodiment, modulation of the TEC can be utilized with direct modulation in the OTDR application. Advantageously, the systems and methods enable use of existing narrow-line width sources in optical fiber systems such as service channels and/or channel transceivers to perform OTDR functionality with performances in line with separate commercial OTDR devices with broad spectrum light sources.

Figure 1:
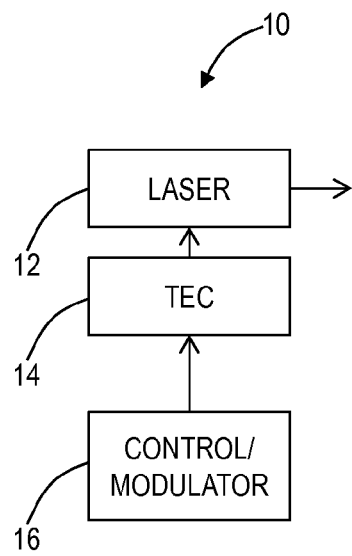
FIG. 1 is a block diagram of a narrow line-width system with reduced coherence effects.

Referring to FIG. 1, in an exemplary embodiment, a block diagram illustrates a narrow line-width system 10 with reduced coherence effects. The system 10 includes a narrow line-width laser source 12, a thermoelectric cooler (TEC) 14, and a controller/modulator 16. As described herein, the narrow line-width source can be ITLA sources, EML sources, DFB sources, and the like. The narrow line-width source can have a line-width in the range of few hundred kHz to a few MHz. In an exemplary embodiment, the laser source 12 can be associated with an existing device in an optical communication system such as an optical service channel transmitter, a channel card transmitter, etc. The thermoelectric cooler 14 is a circuit device that is configured to regulate the wavelength output of the laser source 12. Specifically, the thermoelectric cooler 14 can be thermally coupled to the laser source 12. Generally, the wavelength of light output from the laser source 12 is inversely related to a temperature of the laser source 12. Accordingly, by changing the temperature of the thermoelectric cooler 14, the wavelength of the light output of the laser source 12 can be altered. The controller/modulator 16 is coupled to the thermoelectric cooler 14 for control thereof. The temperature of the thermoelectric cooler 14 is adjusted in response to the input from the controller/modulator 16. Typically, the thermoelectric cooler 14 can control the temperature of the laser source 12 within a certain range, e.g. 15-45 deg. C. The controller/modulator 16 can apply a current, a voltage, a control signal, etc. to the thermoelectric cooler 14 to provide precise incremental changes in temperature of the thermoelectric cooler 14. In operation, the thermoelectric cooler 14 and the controller/modulator 16 can be used in a feedback loop to lock the wavelength of the light output of the laser source 12. Exemplary descriptions of this laser control are described in commonly assigned U.S. Pat. No. 5,943,152 issued Aug. 24, 1999 and entitled "LASER WAVELENTH CONTROL DEVICE" and in commonly assigned U.S. Pat. No. 5,875,273 issued Feb. 23, 1999 and entitled "LASER WAVELENTH CONTROL UNDER DIRECT MODULATION," the contents of each are incorporated by reference herein.

In various exemplary embodiments, the system 10 can be configured such that the controller/modulator 16 modulates or dithers the thermoelectric cooler 14 to shift wavelength of the light output of the laser source 12 for a reduction of the coherence effect. By modulating/dithering the thermoelectric cooler 14, the narrow line-width laser source 12 is artificially broadened on a time average basis to reduce coherent noise. That is, a modification to the thermoelectric cooler 14 can provide an efficient way to randomize the coherent effect. In an exemplary embodiment, the system 10 can be used in a narrow line-width OTDR application. The system 10 can be used as an OTDR with performance in line with commercial broad spectrum OTDR devices at significant cost advantages (i.e., narrow line-width sources versus broad spectrum sources) as well as the fact that narrow line-width sources are typically already found in deployed optical systems (i.e., service channels, channel cards, etc.). The controller/modulator 16 can provide any type of random modulation or dithering to the thermoelectric cooler 14. In an exemplary embodiment, the controller/modulator 16 can provide a square or sinusoidal modulation signal at a relatively low frequency (1-200 Hz), and each showed similar performance.

Assume the thermoelectric cooler 14 has a baseline current input signal of 200 mA, in an exemplary embodiment, the controller/modulator 16 can dither the thermoelectric cooler 14 by +/−20 mA at a frequency of 2 Hz. Additionally, the controller/modulator 16 can also work with an existing wavelength locking feedback loop of the thermoelectric cooler 14. For example, the controller/modulator 16 can provide two functions including monitoring and adjusting the light output of the laser source 12 in a feedback loop and concurrently dithering the thermoelectric cooler 14 to adjust the light output of the laser source 12 reducing coherence. Note, the system 10 is contemplated for use with another system, such as narrow line-width OTDR systems 20, 22 of FIGS. 2-3 or any other systems with modulators, pulse generators, etc.

Figure 2:
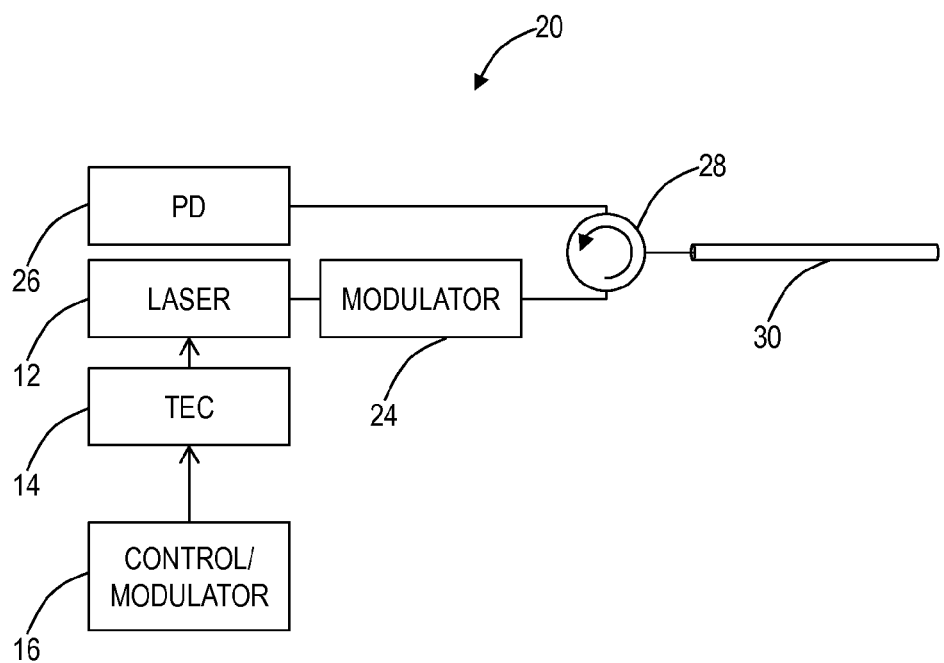
FIG. 2 is a block diagram of a narrow line-width OTDR system with reduced coherence effects with external modulation.
Figure 3:
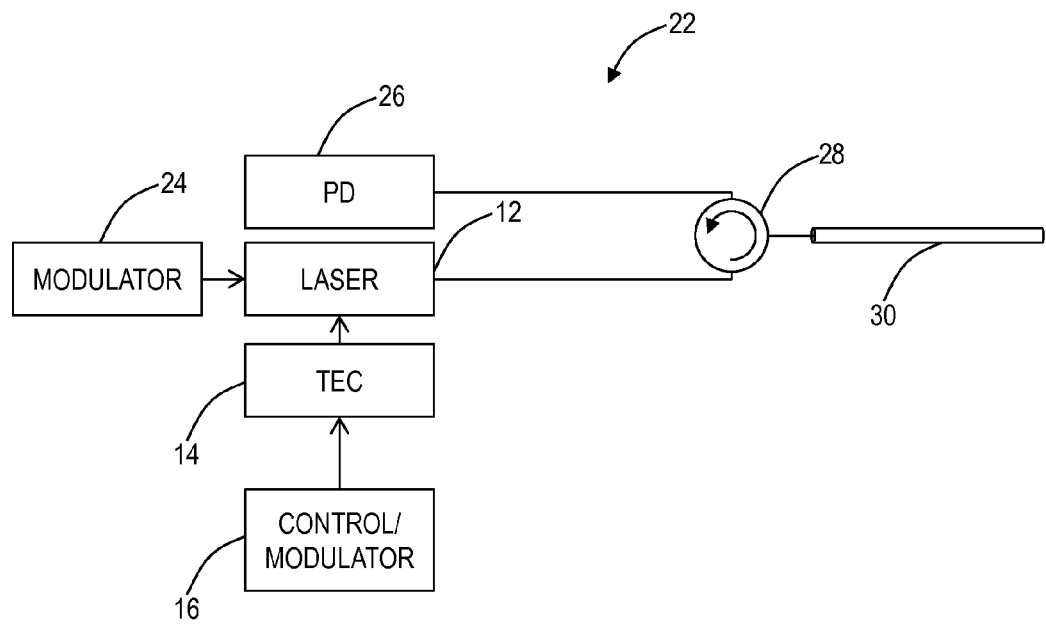
FIG. 3 is a block diagram of a narrow line-width OTDR system with reduced coherence effects with direct modulation.

Referring to FIGS. 2-3, in exemplary embodiments, block diagrams illustrate narrow line-width OTDR systems 20, 22 with reduced coherence effects. The systems 20, 22 include the laser source 12, the thermoelectric cooler 14, the controller/modulator 16, a modulator 24, and a photo-detector 26. The systems 20, 22 can also include a circulator 28 or some other three port device coupling the photo-detector 26 and the laser source 12 to an optical fiber 30. As described herein, the narrow line-width source can be ITLA sources, EML sources, DFB sources, and the like. In FIG. 2, the system 20 is externally modulated with the modulator 24 placed after the laser source 12. Here, the modulator 26 can be an Acousto-Optic (AO) modulator, a Lithium niobate (LiNbO$_3$) modulator, a Mach-Zehnder interferometer, and the like. In FIG. 3, the system 22 is directly modulated with the modulator 24 driving the laser source 12. For an OTDR, the modulator 24 is configured to provide optical pulses, and there is a correlation between pulse width and OTDR resolution. For example, in FIG. 3, the modulator 24 can simply be a drive signal (and associated devices for creating the drive signal) applied to the laser 12 for direct modulation. Of course, shorter pulse widths reduce the overall distance the pulses can travel on the fiber 30. In an exemplary embodiment, for external modulation, the modulator 24 is configured to provide pulses with widths as small as 30 ns. For direct modulation, the modulator 24 is configured to provide pulses with widths as small as 100 ns.

In an exemplary embodiment, the systems 20, 22 can be OTDR systems with the laser source 12 being a narrow line-width source. Here, the systems 20, 22 are an optoelectronic instrument used to characterize the fiber 30. As an OTDR, the laser 12 in conjunction with the modulator 24 is configured to inject a series of optical pulses with a predetermined pulse width to the fiber 30 (i.e., the fiber 30 can be referred to as a fiber under test, device under test, etc.). The photo-detector 26 is configured to extract, from the same end of the fiber 30, light that is scattered (Rayleigh backscatter) or reflected back from points along the fiber. The strength of the return pulses is measured and integrated as a function of time, and is plotted as a function of fiber length. From this, a graph can be obtained providing a measure of the quality of the fiber 30. In the graph, peaks and a slope can be detected therein. Peaks are indicative of discontinuities in the fiber 30 (e.g., poor splices, connectors, etc.) and are a result of reflections therefrom. The slope is indicative of a monitored rate at which the backscatter energy decreases and this can be used to establish the attenuation of each portion of the fiber 30.

The OTDR systems 20, 22 can include the narrow line-width system 10 of FIG. 1. In particular, the systems and methods described herein note that direct modulation and/or dithering of the TEC 14 dramatically reduces noises in OTDR traces (i.e., to levels comparable to commercial broad spectrum OTDRs). Further, direct modulation and/or dithering of the TEC 14 can be used to improve measurement on fiber loss and reflection detection. In an exemplary embodiment, the OTDR systems 20, 22 could alleviate the need for external OTDRs as the components of the systems 20, 22 are typically already present in deployed optical communication systems. For example, the systems 20, 22 could be included in existing Optical Service Channels (OSCs), existing channel line cards, etc. These devices could be integrated within these existing devices providing OTDR functionality in addition to their regular functionality. In an exemplary embodiment, Raman amplifiers could include DFB lasers used for signaling between adjacent Raman amplifiers. These DFB lasers could also be used in the systems 20, 22 providing OTDR functionality.

Figure 4:
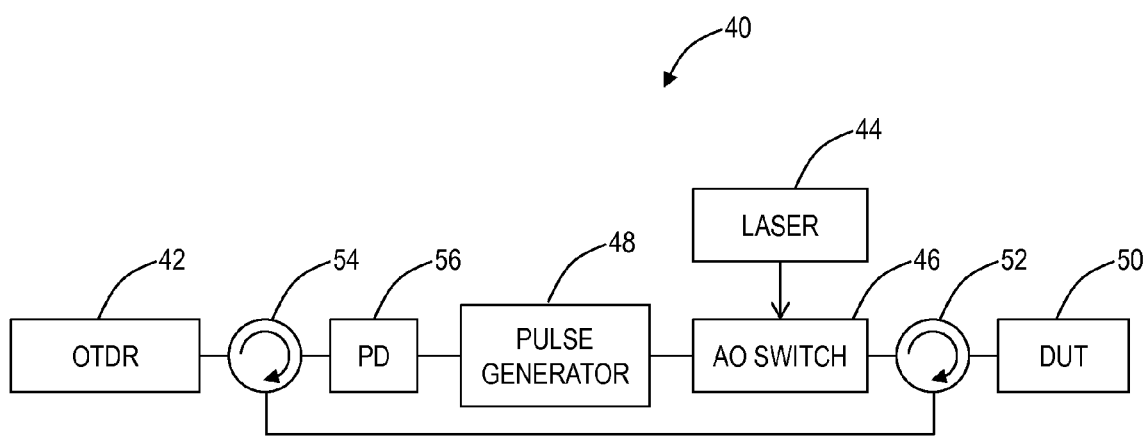
FIG. 4 is a block diagram of a test system for characterizing a narrow line-width OTDR relative to a commercial wide spectrum OTDR.

Referring to FIG. 4, in an exemplary embodiment, a block diagram illustrates a test system 40 for characterizing a narrow line-width OTDR relative to a commercial wide spectrum OTDR 42. In the test system 40, the narrow line-width OTDR is formed through a laser 44, an Acousto-Optic (AO) switch 46, and/or a pulse generator 48. The laser 44 includes the TEC 14 thermally coupled thereto and the TEC 14 is modulated/dithered at various different amplitudes and frequencies as discussed below. The system 20, i.e. an externally modulated narrow line-width OTDR, is formed by the laser 44 and the AO switch 46 as an external modulator. The system 22, i.e. a directly modulated narrow line-width OTDR, is formed by the laser 44 driven by the pulse generator 48. The system 40 includes a device under test 50 which include optical fiber of varying lengths (i.e., single mode fiber (SMF) of 20 m, 3 m, 5 m, 1 m, 25 km, 10 km, and 25 km). The system 40 also includes two circulators 52, 54 and a photo-detector 56. In a test setup, the commercial wide spectrum OTDR 42 is used to trigger the narrow line-width OTDR. The narrow line-width OTDR is set with the same pulse width and pulse interval as the commercial wide spectrum OTDR 42. For the system 22, the AO switch 46 is bypassed when directly modulating the laser 44 (which can be a DFB Transmitter Optical Sub-Assembly (TOSA). Reflected signals from the DUT 50 go through the two circulators 52, 544 back to the photo-detector 56.

Figure 5:
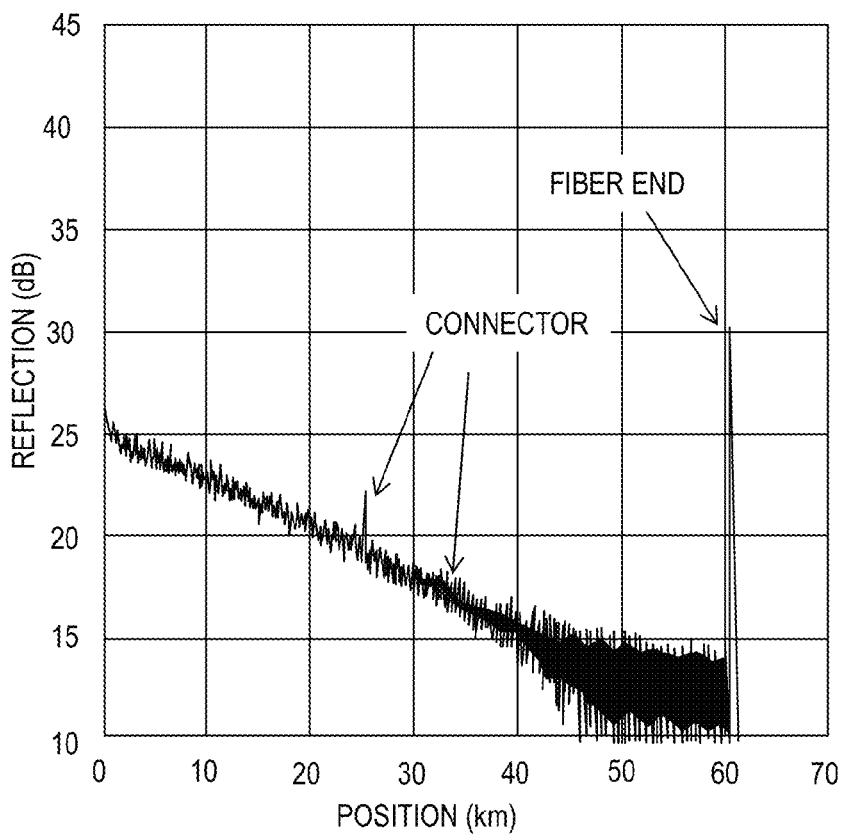
FIG. 5 is an OTDR trace of a baseline configuration of a externally modulated narrow line-width OTDR with a 30 ns pulse width.
Figure 6:
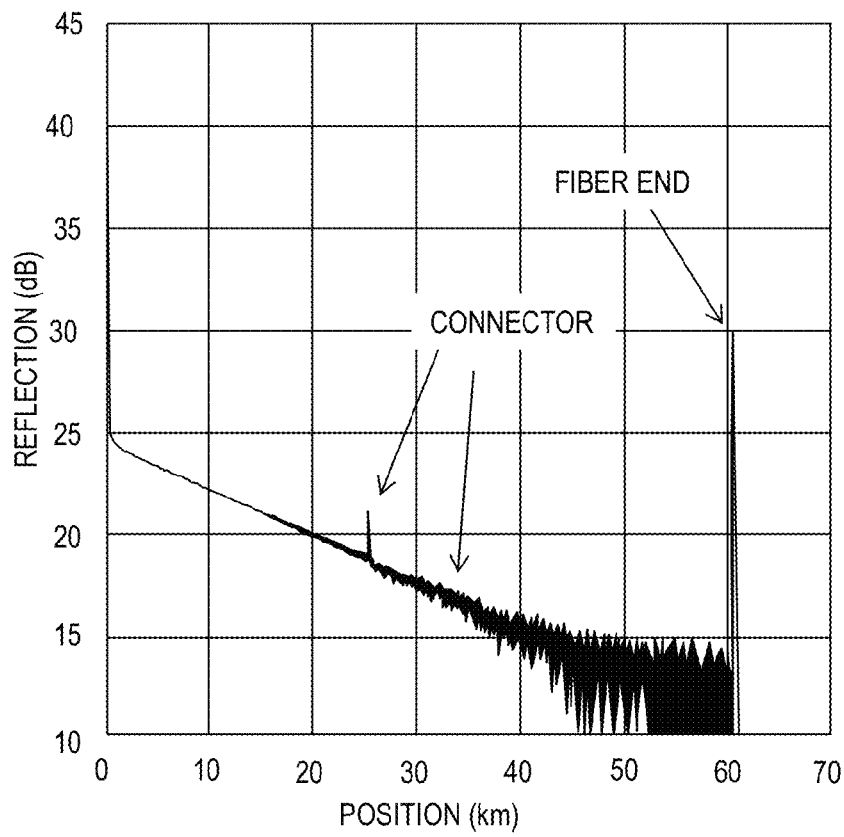
FIG. 6 is an OTDR trace of TEC dithering of the externally modulated narrow line-width OTDR with a 30 ns pulse width.

Referring to FIGS. 5-17, in various exemplary embodiments, graphs illustrate exemplary outputs from the test system 40. FIGS. 5-11 are OTDR traces showing reflection in dB versus position in the DUT 50. Specifically, FIGS. 5-11 illustrate comparisons of a baseline configuration versus a TEC dithering configuration of 40 mA at 2 Hz. The baseline configuration is the laser 44 (i.e., a narrow line-width source—DFB TOSA) externally modulated by the AO switch 46. In each of FIGS. 5-11, there are optical connectors at about 25 km and 35 km and the fiber ends at 60 km. FIGS. 5 and 6 are 30 ns pulse widths which limit the distance in which the OTDR trace provides reasonable results to about 30 km. FIG. 5 is the baseline configuration, and FIG. 6 is the TEC dithering configuration. As can be seen comparing FIG. 6 to FIG. 5, the TEC dithering significantly improves the resolution of the OTDR trace, and the TEC dithering provides comparable performance to the commercial wide spectrum OTDR 42.

Figure 7:
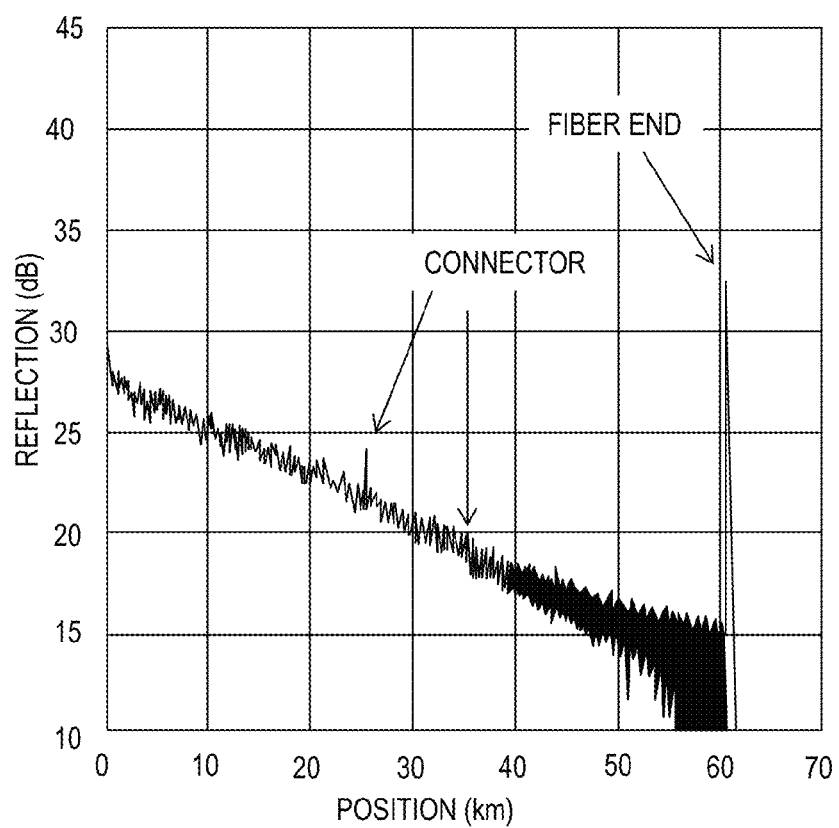
FIG. 7 is an OTDR trace of a baseline configuration of a externally modulated narrow line-width OTDR with a 100 ns pulse width.
Figure 8:
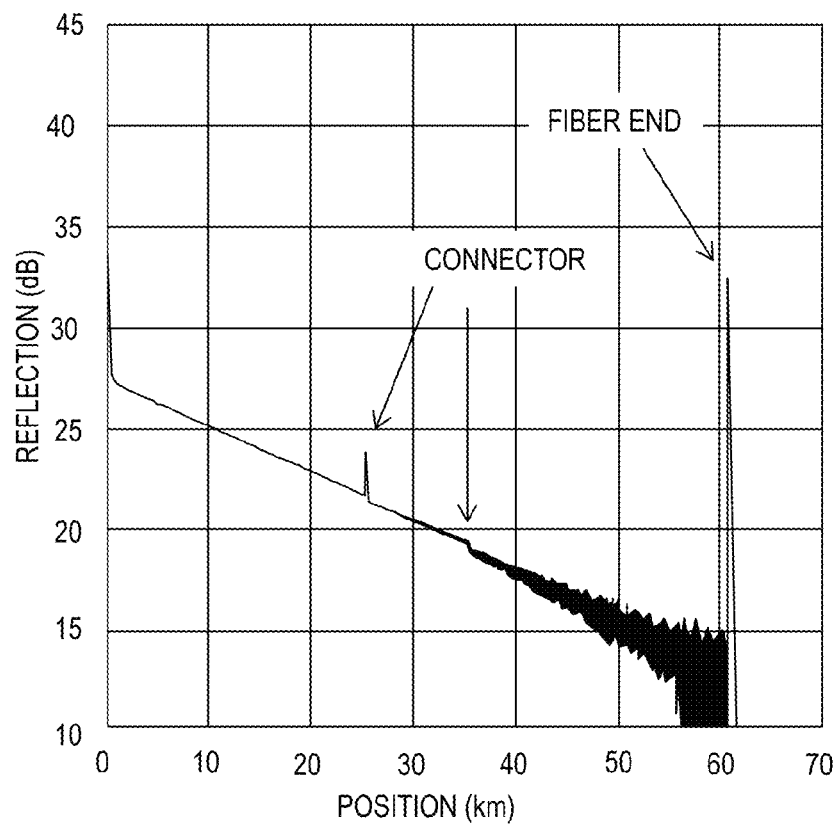
FIG. 8 is an OTDR trace of TEC dithering of the externally modulated narrow line-width OTDR with a 100 ns pulse width.
Figure 9:
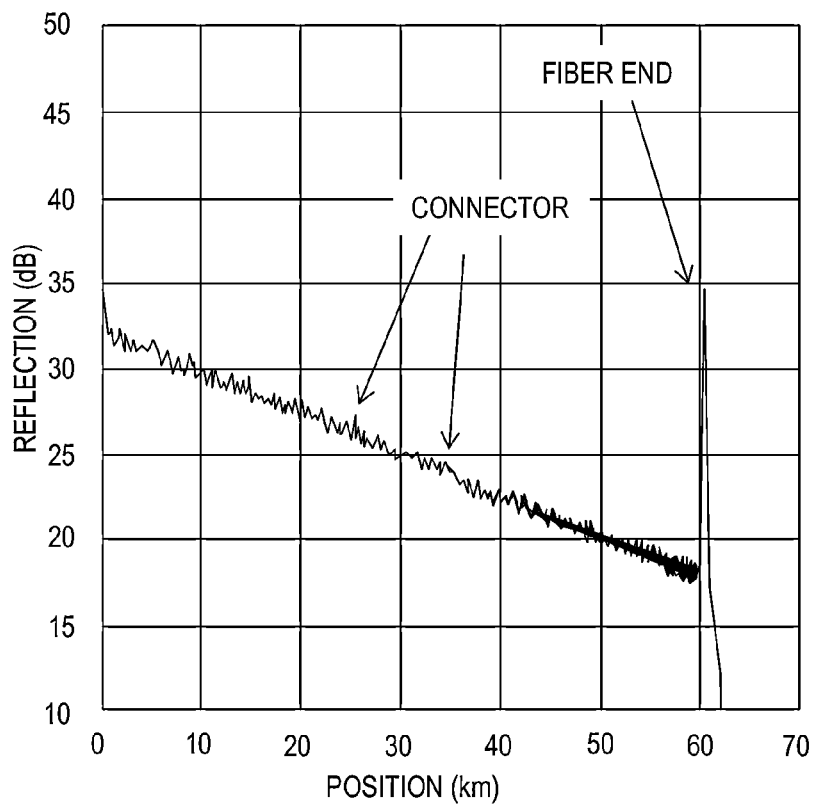
FIG. 9 is an OTDR trace of a baseline configuration of a externally modulated narrow line-width OTDR with a 1 µs pulse width.
Figure 10:
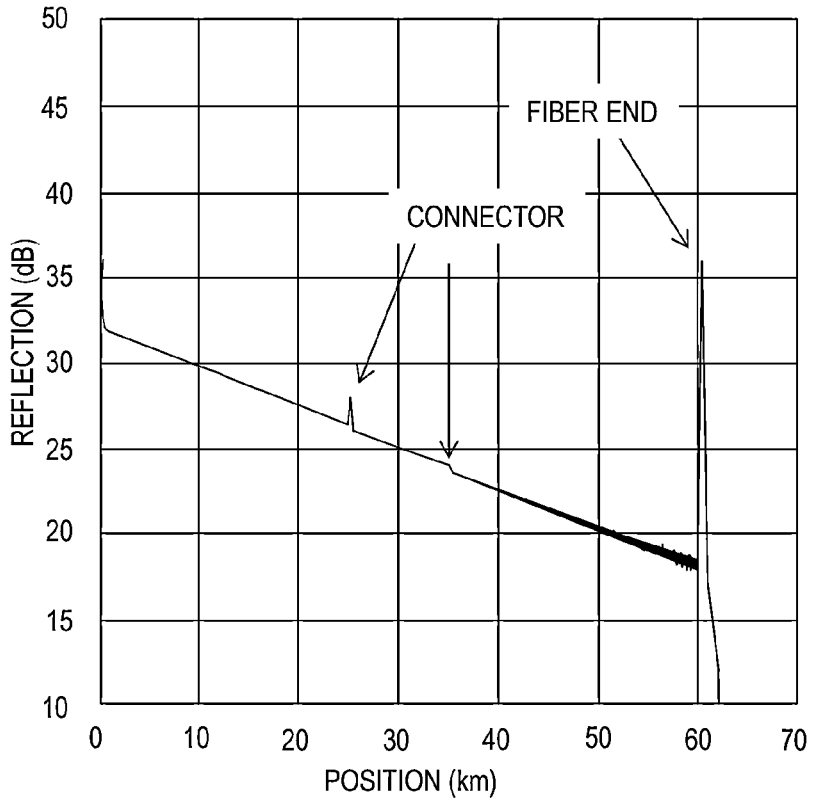
FIG. 10 is an OTDR trace of TEC dithering of the externally modulated narrow line-width OTDR with a 1 µs pulse width.

FIGS. 7 and 8 are 100 ns pulse widths which limit the distance in which the OTDR trace provides reasonable results to about 40 km. FIG. 7 is the baseline configuration, and FIG. 8 is the TEC dithering configuration. As can be seen comparing FIG. 8 to FIG. 7, the TEC dithering significantly improves the resolution of the OTDR trace, and the TEC dithering provides comparable performance to the commercial wide spectrum OTDR 42. Also, direct modulation was performed as well (with and without the TEC dithering), and the direct modulation also provided comparable performance to the commercial wide spectrum OTDR. As can be seen in FIG. 8, the connectors are easy to identify due to the reflections at 25 km and 35 km. Further, the TEC dithering in FIG. 8 provides significantly better resolution than the baseline configuration. FIGS. 9 and 10 are 1 μs pulse widths with FIG. 9 as the baseline configuration and FIG. 10 as the TEC dithering configuration. As can be seen comparing FIG. 10 to FIG. 9, the TEC dithering significantly improves the resolution of the OTDR trace, and the TEC dithering provides comparable performance to the commercial wide spectrum OTDR 42. Also, direct modulation was performed as well (with and without the TEC dithering), and the direct modulation also provided comparable performance to the commercial wide spectrum OTDR. As can be seen in FIG. 10, the connectors are easy to identify due to the reflections at 25 km and 35 km. Further, the TEC dithering in FIG. 10 provides significantly better resolution than the baseline configuration.

Figure 11:
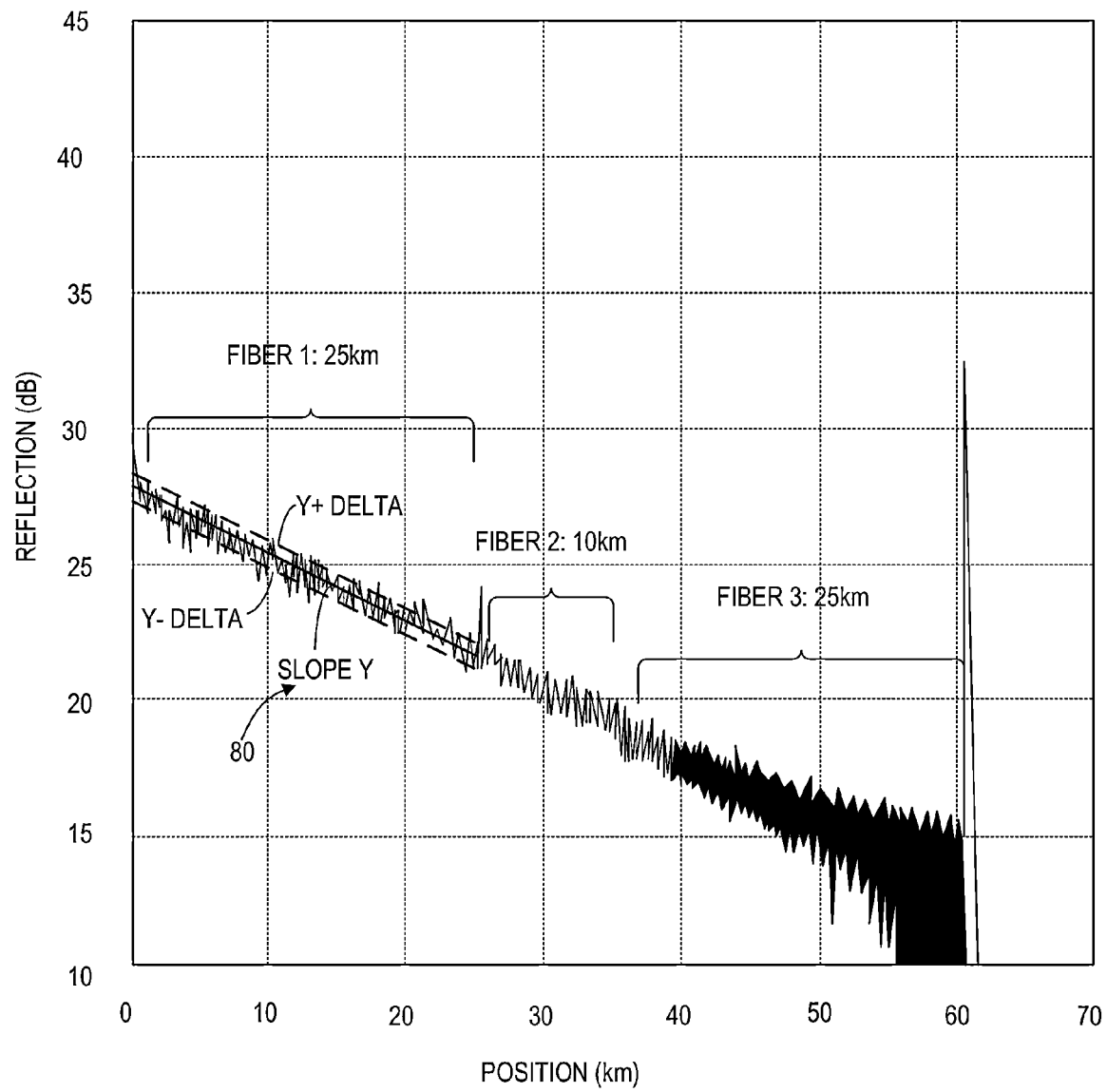
FIG. 11 is the OTDR trace of FIG. 7 illustrating a methodology to quantify OTDR trace quality.
Figure 12:
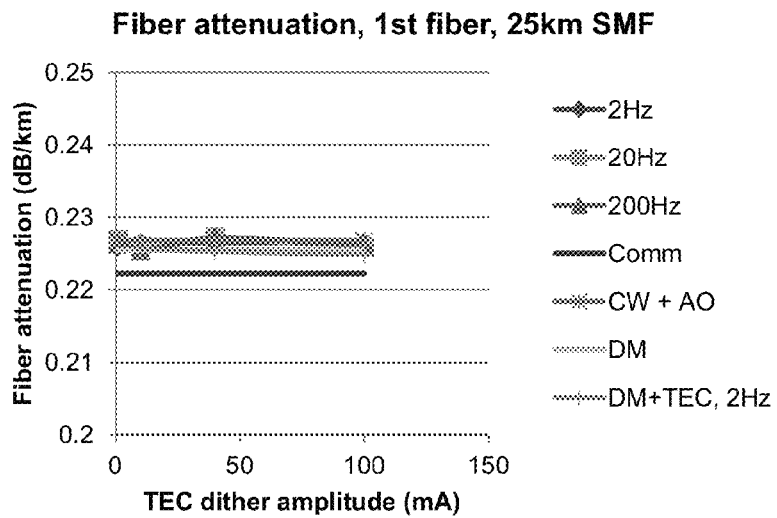
FIGS. 12-14 are fiber loss graphs showing fiber attenuation (dB/km) versus TEC dither amplitude for different configurations over different fibers.
Figure 13:
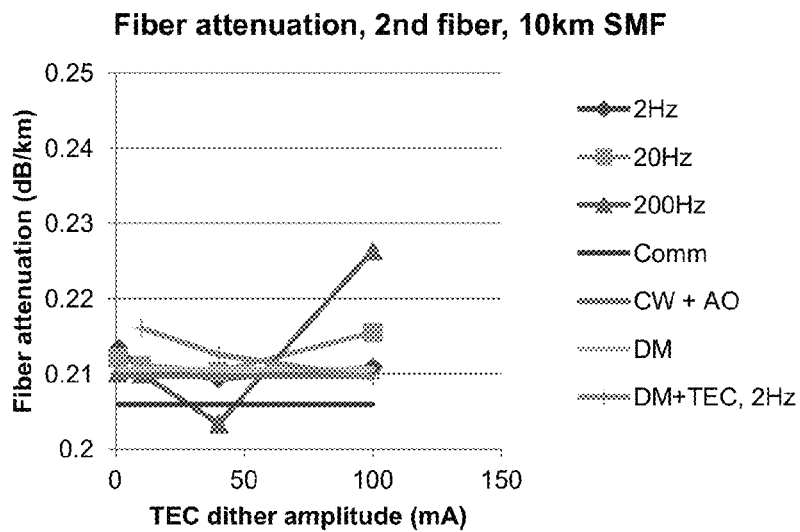
Figure 14:
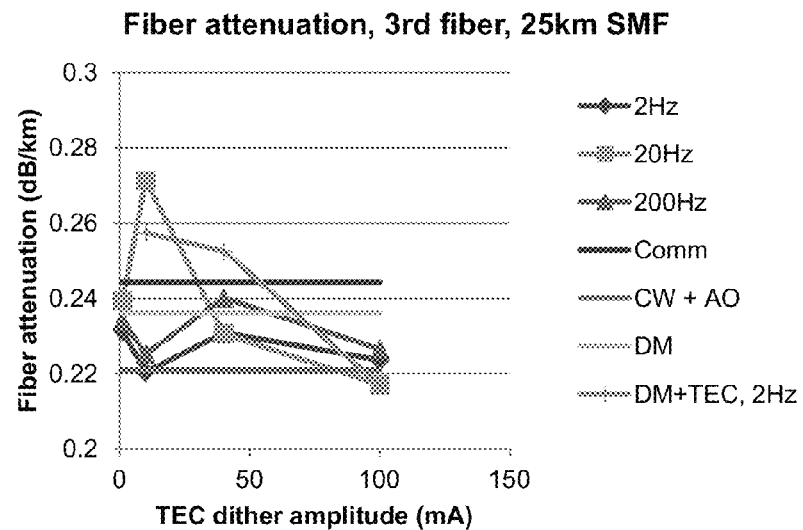
Figure 15:
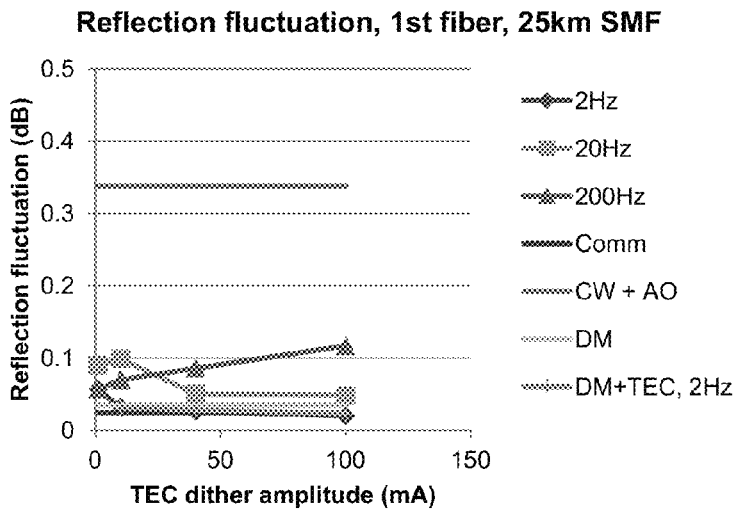
FIGS. 15-17 are reflection fluctuation graphs using the methodology described above in FIG. 11 to characterize the reflection fluctuations.
Figure 16:
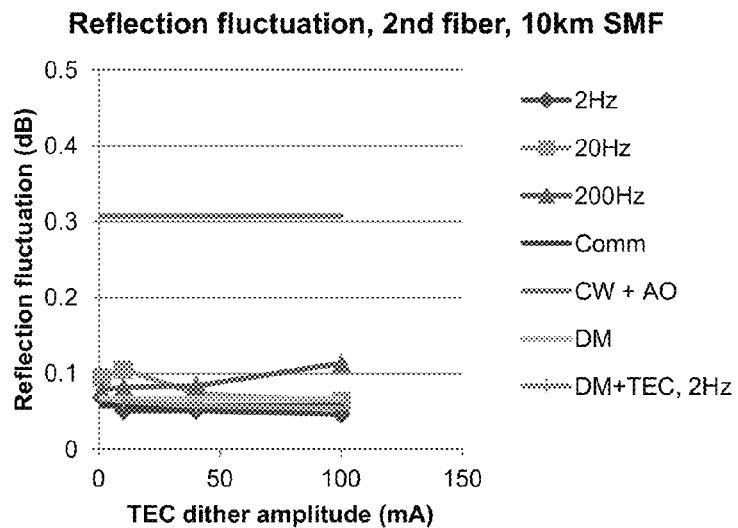
Figure 17:
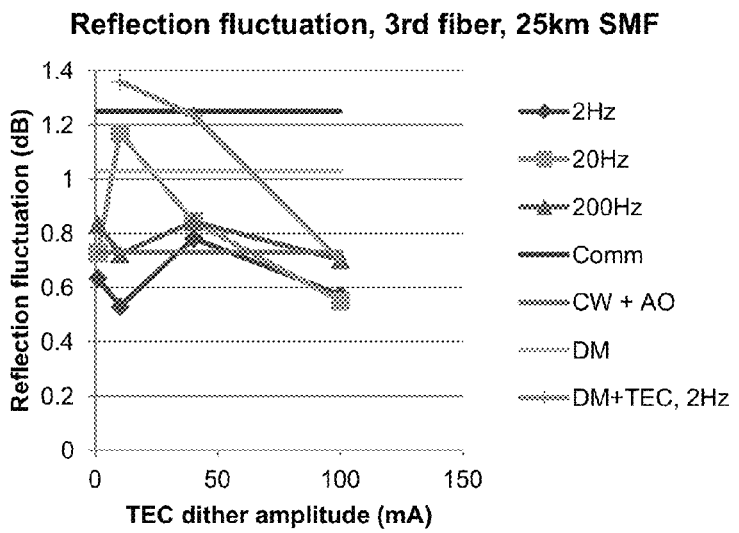

FIG. 11 is the same OTDR trace as FIG. 7 and is illustrated to describe a methodology to quantify OTDR trace quality. In each of the FIGS. 5-17, the fiber includes three long pieces of SMF fiber including a first fiber of 25 km, a second fiber of 10 km, and a third fiber of 25 km. The splicing/connectors are shown in FIGS. 5-11 with the connectors at 25 km and 35 km. Each piece of fiber includes a slope 80 of the backscatter reflections. This slope (Y) 80 is the fiber loss. OTDR trace quality can be defined by a delta and Y+/−delta contains at least 50% of predictions. FIGS. 12-17 illustrate fiber loss and OTDR trace quality for the 100 ns pulse using several different configurations. FIGS. 12-14 are fiber loss graphs showing fiber attenuation (dB/km) versus TEC dither amplitude for the different configurations. FIGS. 15-17 use the methodology described above in FIG. 11 to characterize the reflection fluctuations. In particular, these graphs are reflection fluctuation (dB) versus TEC dither amplitude. The configurations include TEC dithering at 2 Hz (2 Hz), TEC dithering at 20 Hz (20 Hz), TEC dithering at 200 Hz (200 Hz), the commercial wide spectrum OTDR (Comm), the baseline configuration of a CW laser externally modulated with the AO switch (CW+AO), a directly modulated narrow line-width configuration (DM), and a directly modulated narrow line-width configuration plus TEC dithering at 2 Hz (DM+TEC, 2 Hz). Note, the X-axis is TEC dither amplitude (mA) and this does not vary in the Comm, CW+AO, and DM configurations as these do not include TEC dithering.

As can be seen in FIGS. 12-14, fiber loss estimation is fairly accurate with the 100 ns pulse up to about 35 km. While not shown, the fiber loss estimation is quite accurate with the 30 ns pulse to within 25 km, and the fiber loss estimation is very accurate with the 1 μs pulse along the 60 km of the fiber. As can be seen in FIGS. 15-17, the OTDR trace is clean over 35 km except for the CW+AO baseline configuration. With the 100 ns pulse, the narrow line-width systems can detect reflection or discontinuities over 0.4 dB within 35 km, and the baseline configuration can over do over 2 dB. Similarly, the 30 ns pulse can detect reflection or a discontinuity over 0.4 dB within 25 km with the narrow line-width systems, and the 1 μs pulse can detect reflection or a discontinuity over 0.4 dB within 35 km with the narrow line-width systems within 60 km.

Figure 18:
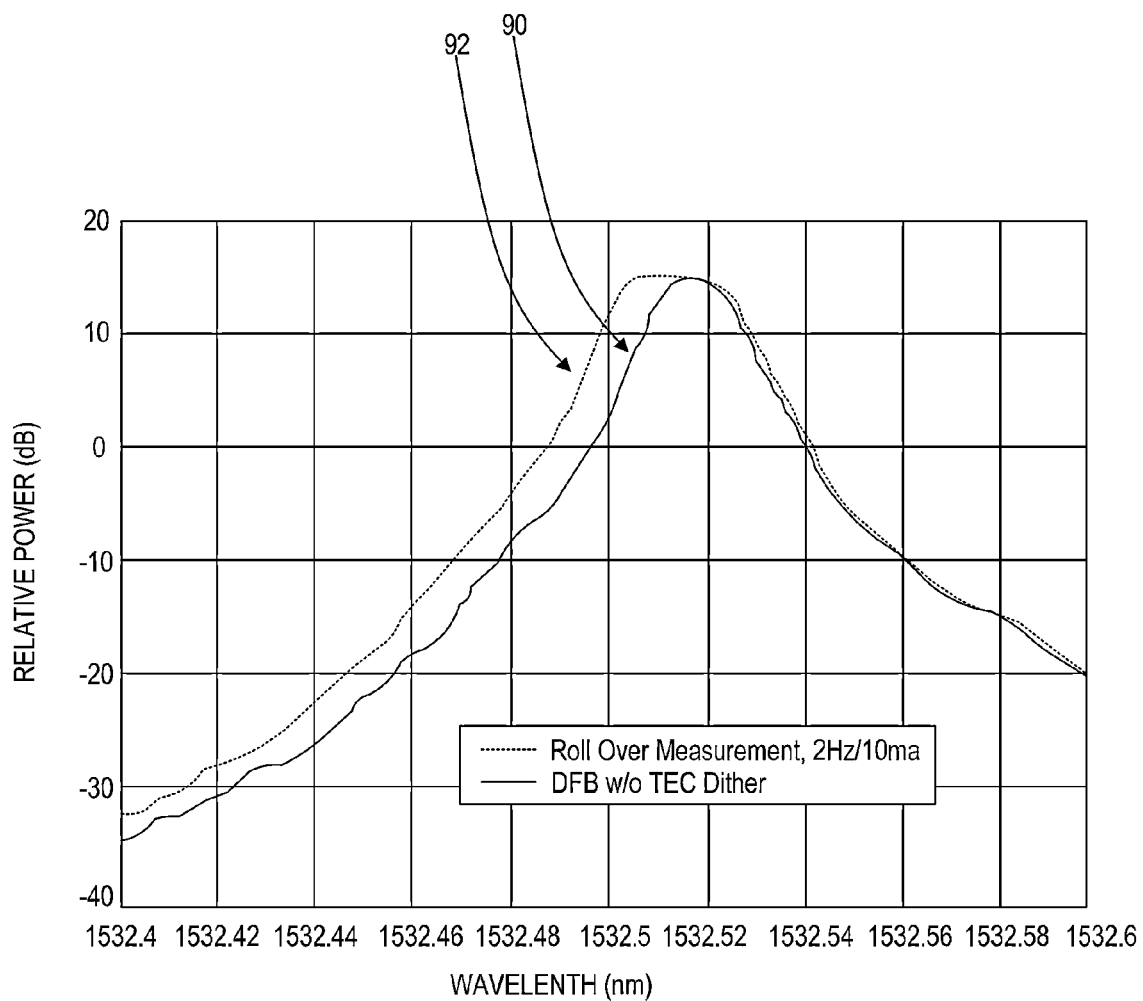
FIG. 18 is a spectral graph of the line-width of a DFB laser source without TEC dither versus the line-width of the DFB laser source with TEC dither at 10 mA over 2 Hz.

Referring to FIG. 18, in an exemplary embodiment, a spectral graph illustrates the line-width of a DFB laser source without TEC dither 90 versus the line-width of the DFB laser source with TEC dither 92 at 10 mA over 2 Hz. As can be seen in FIG. 18, even a modest dithering of the TEC at 10 mA over 2 Hz broadens the time-averaged spectral line-width of a narrow line-width source thereby reducing coherence.

Figure 19:
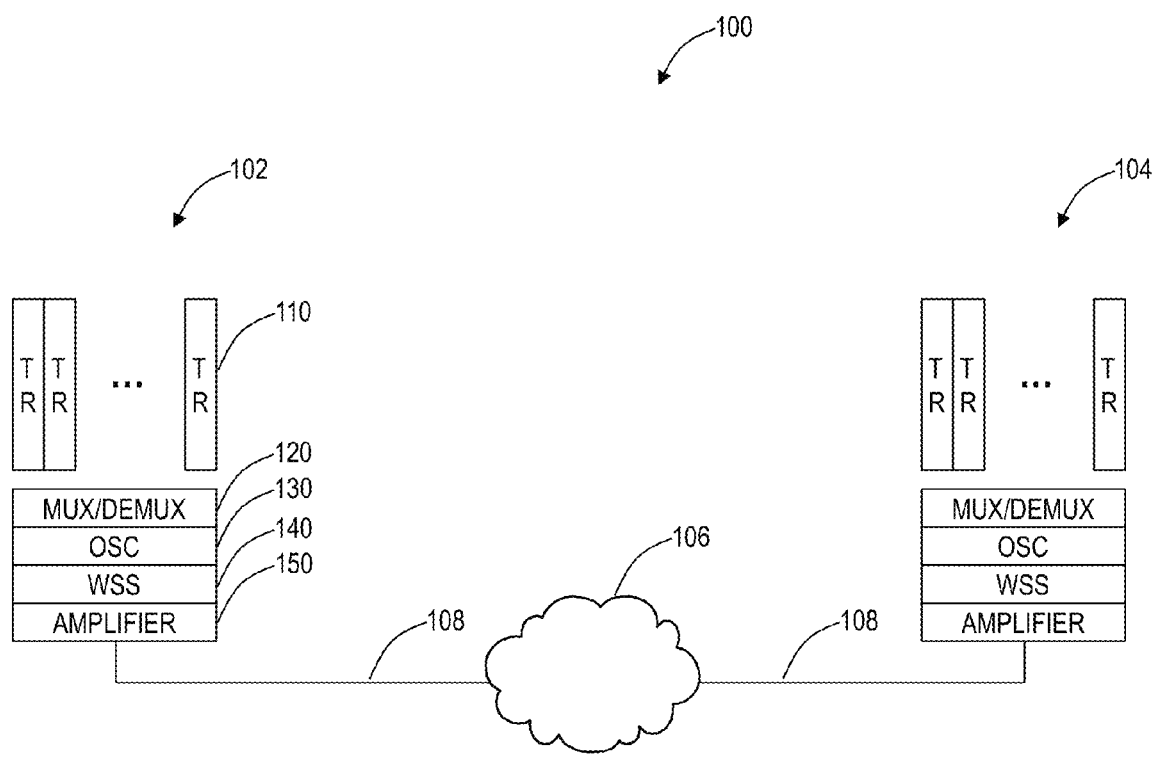
FIG. 19 is a block diagram of an optical transport system which can utilize the narrow line-width OTDR.

Referring to FIG. 19, in an exemplary embodiment, a block diagram illustrates an optical transport system 100. The optical transport system 100 includes an optical node 102 communicatively coupled to an optical node 104 through an optical network 106. The optical nodes 102, 104 are interconnected in a linear fashion over optical fiber 108. The optical network 106 includes various components, elements, devices, etc. that are omitted for illustration purposes. For example, the optical network 106 can include amplifiers, optical add/drop multiplexers (OADMs), reconfigurable OADMs (ROADMs), regenerators, etc. Also, the optical transport system 100 is illustrated with only the optical nodes 102, 104 for illustration purposes, and those of ordinary skill in the art will recognize the optical transport system 100 can include additional nodes and the like. For example, the optical nodes 102, 104 are single degree nodes, and those of ordinary skill in the art will recognize that the optical nodes 102, 104 can be expanded to multiple degrees as well as having other nodes to form a meshed optical network.

The optical nodes 102, 104 can include transceivers 110, multiplexers/demultiplexers (MUX/DEMUX) 120, an optical service channel (OSC) 130, a wavelength selective switch (WSS) 140, and one or more amplifiers 150. These various components/devices 110, 120, 130, 140, 150 can physically realized as modules, line cards, etc. Also, the modules, line cards, etc. can combine the functionality of the various components/devices 110, 120, 130, 140, 150 or the various components/devices 110, 120, 130, 140, 150 can be realized separately. Those of ordinary skill in the art will recognize the optical nodes 102, 104 can include other components which are omitted for illustration purposes, and that the systems and methods described herein are contemplated for use with a plurality of different network elements for use in optical networks with the optical nodes 102, 104 presented as an exemplary type of network element. The transceivers 110 are interfaces that enable client devices (not shown) to communicate over the optical transport system 100. For example, the transceivers 110 can be transponders, muxponders, etc. In an exemplary embodiment, the transceivers 110 can include a plurality of physical ports thereon with client facing ports that are short reach and line facing ports that include dense wave division multiplexing (DWDM) wavelengths and modulation formats. For example each of the ports can include a signal at 10 Gbps, 40 Gbps, 100 Gbps, etc. The multiplexers/demultiplexers 120 are optical filtering devices enabling multiple wavelengths from the transceivers 110 to be physically combined/split. The WSS 140 provides selective add/drop or express of wavelengths in the optical transport system 100. The WSS 140 is typically used in meshed interconnected systems with varying degrees at the nodes. In an example such as a point-to-point system as illustrated in FIG. 19, the WSS 140 can be omitted.

The OSC 130 is a service channel allowing all-optical devices to communicate with one another with respect to operations, administration, maintenance, and provisioning (OAM&P) data. The OSC 130 can also be referred to as an optical supervisory channel. The OSC 130 is typically an additional wavelength usually outside the Erbium Doped Fiber Amplifier (EDFA) amplification band (e.g., at 1510 nm, 1620 nm, 1310 nm or another proprietary wavelength). The OSC carries information about the multi-wavelength optical signal as well as remote conditions at the optical nodes 102, 104, amplifier sites, etc. Unlike the DWDM client signal-carrying wavelengths from the transceivers 110, the OSC 130 is always terminated at intermediate amplifier sites, where it receives local information before retransmission. The amplifier 150 can be one or more EDFA devices, Raman amplifiers, Semiconductor optical amplifiers, and the like. An EDFA device can provide amplification of wavelengths between approximately 1530 nm and 1560 nm (referred to as the "C" band). The Raman amplifier can include physically pumping the fiber 108 in co-directional pumping, contra-directional pumping, or both. Additionally, the Raman amplifier can also include a separate OSC wavelength for operations associated with the Raman amplifier. Of note, the optical transport system 100 (as well as any generalized optical transport system) includes various narrow line-width sources. For example, the transceivers 110, the OSC 130, Raman amplifier OSC, etc. Conventionally, OTDR devices to test the fiber 108 are separate devices from the various components in the optical transport system 100 or components integrated within the optical transport system 100 but whose function is solely dedicated to OTDR. Using the systems and methods described herein, OTDR performance is significantly improved with narrow line-width sources.

In an exemplary embodiment, one of the components/devices 110, 120, 130, 140, 150 could be configured with an integrated OTDR using a narrow line-width source. For example, another wavelength outside the amplification band and separate from any OSC wavelengths used could be dedicated within the optical transport system 100 for performing OTDR functionality on-demand, periodically, or continuously. In another exemplary embodiment, one of the components/devices 110, 120, 130, 140, 150 could be configured to perform OTDR functionality in addition to providing other functionality in the optical transport system 100. For example, the Raman amplifier's OSC could also be configured as an OTDR system using the systems and methods described herein. Alternatively, the OSC 130, the transceivers 110, etc. could also perform OTDR functionality on-demand.

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure and are intended to be covered by the following claims.

What is claimed is:

1. An optical time domain reflectometer (OTDR) system, comprising:
    a narrow line-width laser source comprising a thermoelectric cooler thermally coupled thereto;
    a modulator configured to modulate the narrow line-width laser source;
    a device configured to couple an output of the narrow line-width laser source and the modulator to a device under test and an input from the device under test to a photo-detector; and
    a controller configured to provide an input signal to the thermoelectric cooler to monitor and adjust a light output of the narrow line-width laser source in a wavelength locking feedback loop and to concurrently dither the thermoelectric cooler to adjust the light output of the narrow line-width laser source by about 0.02 nm and reduce coherence to reduce noise in OTDR traces to levels comparable to a wide spectrum laser source OTDR;
    wherein the narrow line-width laser source, the thermoelectric cooler, and the controller are disposed in a channel line card that is a channel transceiver connected to a multiplexer configured to combine a Dense Wavelength Division Multiplexing (DWDM) output from the modulator in an optical communication system and are collectively configured to perform OTDR functionality in the optical communication system.

2. The optical time domain reflectometer system of claim 1, wherein the modulator comprises an external modulator.

3. The optical time domain reflectometer system of claim 2, wherein the input signal is varied to the thermoelectric cooler to reduce coherence of the narrow line-width laser source.

4. The optical time domain reflectometer system of claim 1, wherein the modulator directly modulates the narrow line-width laser source.

5. The optical time domain reflectometer system of claim 1, wherein the input signal is varied to the thermoelectric cooler to reduce the effects of the coherence of the narrow line-width laser source.

6. The optical time domain reflectometer system of claim 4, wherein the controller is configured to adjust the varied input signal at a predetermined frequency and for predetermined amount of change in the thermoelectric cooler.

7. The optical time domain reflectometer system of claim 1, wherein the narrow line-width laser source comprises a line-width of 10 MHz or less with a time averaged line-width artificially broadened responsive to the varied input signal to the thermoelectric cooler.

8. The optical time domain reflectometer system of claim 1, wherein the narrow line-width laser source comprises one of an Integrable Tunable Laser Assembly (ITLA), an Externally Modulated Laser (EML), and a Distributed Feedback (DFB) laser.

9. An optical apparatus, comprising:
    a narrow line-width laser source;
    a thermoelectric cooler thermally coupled to the narrow line-width laser source; and
    a controller communicatively coupled to the thermoelectric cooler and configured to provide a varied input signal to the thermoelectric cooler and to monitor and adjust a light output of the narrow line-width laser source in a wavelength locking feedback loop and to concurrently dither the thermoelectric cooler to adjust the light output of the narrow line-width laser source by about 0.02 nm and reduce coherence to reduce noise in optical time domain reflectometer (OTDR) traces to levels comparable to a wide spectrum laser source OTDR;

wherein the narrow line-width laser source, the thermoelectric cooler, and the controller are disposed in a channel line card that is a channel transceiver connected to a multiplexer configured to combine a Dense Wavelength Division Multiplexing (DWDM) output from a modulator in an optical communication system and are collectively configured to perform optical time domain reflectometer (OTDR) functionality in the optical communication system.

10. The optical apparatus of claim 9, wherein the narrow line-width laser source comprises a line-width of 10 MHz or less with a time averaged line-width artificially broadened responsive to the varied input signal to the thermoelectric cooler.

11. The optical apparatus of claim 9, wherein the narrow line-width laser source comprises one of an Integrable Tunable Laser Assembly (ITLA), an Externally Modulated Laser (EML), and a Distributed Feedback (DFB) laser.

12. An optical system, comprising:
a first optical node communicatively coupled to a second optical node;
wherein the first optical node comprises:
at least one narrow line-width source, wherein the at least one narrow line-width source comprises a thermoelectric cooler thermally coupled thereto;
a modulator configured to modulate the at least one narrow line-width source; and
a controller configured to provide an input signal to the thermoelectric cooler;
wherein at least one narrow line-width source is configured to perform optical time domain reflectometer (OTDR) functionality between the first optical node and the second optical node;
wherein the at least one narrow line-width source, the thermoelectric cooler, and the controller are disposed in a channel line card that is a channel transceiver connected to a multiplexer configured to combine a Dense Wavelength Division Multiplexing (DWDM) output from the modulator in the first optical node and are collectively configured to perform OTDR functionality in the optical system; and
wherein the controller provides the input signal to the thermoelectric cooler to monitor and adjust a light output of the at least one narrow line-width laser source in a wavelength locking feedback loop and to concurrently dither the thermoelectric cooler to adjust the light output of the at least one narrow line-width laser source by about 0.02 nm and reduce coherence to reduce noise in OTDR traces to levels comparable to a wide spectrum laser source OTDR.

13. The optical system of claim 12, wherein the at least one narrow line-width source comprises a wavelength outside of an amplification band of amplifiers between the first optical node and the second optical node.

14. The optical system of claim 12, wherein the at least one narrow line-width source is a monitor wavelength of a Raman amplifier between the first optical node and the second optical node.

* * * * *